United States Patent
Bouchy

(10) Patent No.: US 10,851,030 B2
(45) Date of Patent: Dec. 1, 2020

(54) USE OF A BIFUNCTIONAL CATALYST BASED ON IZM-2 WITH A SPECIFIC SI/AL RATIO FOR THE ISOMERIZATION OF LONG PARAFFINIC FEEDSTOCKS TO MIDDLE DISTILLATES

(71) Applicant: IFP Energies nouvelles, Rueil-Malmaison (FR)

(72) Inventor: Christophe Bouchy, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/440,272

(22) Filed: Jun. 13, 2019

(65) Prior Publication Data

US 2019/0382323 A1   Dec. 19, 2019

(30) Foreign Application Priority Data

Jun. 15, 2018 (FR) ..................... 18 55286

(51) Int. Cl.
   *C07C 5/27* (2006.01)
   *B01J 29/74* (2006.01)
   *C10G 45/64* (2006.01)

(52) U.S. Cl.
CPC ............ *C07C 5/2708* (2013.01); *B01J 29/74* (2013.01); *C10G 45/64* (2013.01); *B01J 2229/20* (2013.01); *B01J 2229/42* (2013.01); *C07C 2521/04* (2013.01); *C07C 2529/74* (2013.01); *C10G 2300/1081* (2013.01); *C10G 2300/70* (2013.01)

(58) Field of Classification Search
None
See application file for complete search history.

(56) References Cited

U.S. PATENT DOCUMENTS

| | | | |
|---|---|---|---|
| 9,156,748 B2 * | 10/2015 | Bouchy | ................. C07C 5/226 |
| 9,586,828 B2 | 3/2017 | Bouchy et al. | |
| 10,183,902 B2 | 1/2019 | Bouchy | |

FOREIGN PATENT DOCUMENTS

| | | |
|---|---|---|
| FR | 2934794 A1 | 2/2010 |
| FR | 3054454 A1 | 2/2018 |

OTHER PUBLICATIONS

Search Report in corresponding FR 1855286 dated Jan. 28, 2019 (pp. 1-2).

* cited by examiner

*Primary Examiner* — In Suk C Bullock
*Assistant Examiner* — Alyssa L Cepluch
(74) *Attorney, Agent, or Firm* — Millen, White, Zelano & Branigan, PC; Ryan Pool

(57) ABSTRACT

The present invention describes a process for the isomerization of paraffinic feedstocks operating at a temperature of between 200° C. and 500° C., at a total pressure of between 0.45 MPa and 7 MPa, at a hydrogen partial pressure of between 0.3 and 5.5 MPa, at an hourly space velocity of between 0.1 and 10 kilograms of feedstock introduced per kilogram of catalyst and per hour and using a catalyst comprising at least one metal of group VIII of the periodic table of elements, at least one matrix and at least one zeolite IZM-2, in which the ratio between the number of moles of silicon and the number of moles of aluminium of the zeolite IZM-2 network is between 25 and 55, preferably between 25 and 50, and preferably between 30 and 50.

11 Claims, No Drawings

USE OF A BIFUNCTIONAL CATALYST BASED ON IZM-2 WITH A SPECIFIC SI/AL RATIO FOR THE ISOMERIZATION OF LONG PARAFFINIC FEEDSTOCKS TO MIDDLE DISTILLATES

FIELD OF THE INVENTION

In order to meet the demand for middle distillate bases, i.e. a fraction that may be incorporated into the kerosene and/or gas oil pool, various methods for producing middle distillates based on the use of petroleum, natural gas or renewable resources may be used.

Middle distillate bases may thus be produced from a paraffinic feedstock obtained from a feedstock derived from renewable sources, and in particular from plant oils or animal fats, which are raw or which have undergone a pretreatment, and also mixtures of such feedstocks. Specifically, said feedstocks derived from renewable sources contain chemical structures of triglyceride or free fatty acid or ester type, the structure and length of the hydrocarbon-based chain of these feedstocks being compatible with the hydrocarbons present in middle distillates. Said feedstocks derived from renewable sources produce, after hydrotreatment, paraffinic feedstocks that are free of sulfur compounds and of aromatic compounds. These paraffinic feedstocks are typically composed of linear paraffins containing between 9 and 25 carbon atoms.

Middle distillate bases may also be produced from natural gas, coal or renewable sources via the Fischer-Tropsch synthetic process. In particular, the "low-temperature" Fischer-Tropsch synthesis using cobalt catalysts makes it possible to produce essentially paraffinic linear compounds having a very variable number of carbon atoms, typically from 1 to 100 carbon atoms or even more. Separation steps may make it possible to recover paraffinic feedstocks containing between 9 and 25 carbon atoms.

However, these middle distillate bases obtained after hydrotreatment of plant oils or after the low-temperature Fischer-Tropsch synthetic process generally cannot be incorporated as such into the kerosene or gas oil pool in particular on account of insufficient cold properties. Specifically, high molecular weight paraffins which are linear or very sparingly branched and which are present in these middle distillate bases lead to high flow points and thus to congealing for uses at low temperature. For example, the flow point of a linear hydrocarbon containing 20 carbon atoms per molecule and the boiling point of which is equal to about 340° C., i.e. typically within the middle distillate fraction, is about +37° C., which renders its use impossible, the specification being −15° C. for gas oil. In order to lower the flow point values, these linear or very sparingly branched paraffins must be totally or partially removed.

This operation may be performed by extraction with solvents such as propane or methyl ethyl ketone, this process then being referred to as deparaffining with propane or with methyl ethyl ketone (MEK). However, these techniques are expensive, lengthy and not always easy to perform.

Selective cracking of the longest linear paraffinic chains, which leads to the formation of compounds of lower molecular weight, part of which may be removed by distillation, constitutes a solution for reducing the flow point values. Given their shape selectivity, zeolites are among the catalysts most widely used for this type of process. The catalyst that is the most widely used in the deparaffining category by selective cracking is zeolite ZSM-5, of MFI structural type, which has three-dimensional porosity, with medium pores (aperture at 10 oxygen atoms 10MR). However, the cracking brought about in such processes leads to the formation of large amounts of products of lower molecular weights, such as butane, propane, ethane and methane, which considerably reduces the yield of desired products.

Another solution for improving the cold resistance consists in isomerizing long linear paraffins while minimizing the cracking. This may be achieved by performing a hydroisomerization process using difunctional catalysts. The difunctional catalysts involve a Brønsted acid phase (for example a zeolite) and a hydro/dehydrogenating phase (for example platinum) and generally a matrix (for example alumina). The appropriate choice of the acidic phase makes it possible to promote the isomerization of long linear paraffins and to minimize the cracking. Thus, the form selectivity of medium-pore (10MR) one-dimensional zeolites such as zeolites ZSM-22, ZSM-23, NU-10, ZSM-48 and ZBM-30 makes them particularly suitable for use for obtaining catalysts that are selective towards isomerization. These examples illustrate the continuous research carried out in order to develop ever more effective catalysts for the isomerization of long linear paraffins, while minimizing the formation of cracking products through the use of appropriate zeolites.

In addition to the selectivity towards isomerization, the activity of the catalyst is also an important parameter. Increasing the activity of the catalyst makes it possible to improve the overall operation of the process from the point of view of its productivity of its energy consumption. It is therefore desirable to develop catalysts that are as active and selective as possible towards isomerization. The activity of bifunctional isomerization catalysts is to a large extent dependent on the activity of the Brønsted acid phase (for example zeolite), and therefore on its activity, used in said catalysts. The acidity of the zeolite phase is in the end dependent on the number of Brønsted acid sites of said phase and also on their force (C. Marcilly, catalyse acido-basique, volume 1, 2003). One means for increasing the activity of a bifunctional isomerization catalyst can thus be to increase the acidity of the zeolite phase involved in said catalyst by increasing the density of acid sites of the zeolite phase, all things otherwise being equal.

It is however also well known that, for a bifunctional isomerization catalyst, the ratio between the number of sites of the hydro/dehydrogenating phase and the number of sites of the acid phase has an impact on its selectivity towards isomerization. Too great a decrease in this ratio leads to a decrease in the selectivity of the catalyst towards isomerization. This has for example been reported for the isomerization of n-decane on catalysts based on platinum and on zeolite USY (F. Alvarez et al. Journal of Catalysis, 162, 1996, 179). More recently, this has also been reported for the isomerization of n-hexadecane on catalysts based on platinum, on zeolite USY or on zeolite BEA (P. Mendes et al., AIChE Journal, 63, 7, 2017, 2864).

The increase in the activity of the bifunctional catalyst and the maximization of its selectivity towards isomerization therefore requires contradictory demands in terms of acid site density for the zeolite involved in the catalyst.

Recently, the applicant, in its works, has developed a new zeolite, zeolite IZM-2 as described in application FR 2 918 050 A, and also a process for converting long paraffinic feedstocks having a number of carbon atoms of between 9 and 25 using a catalyst comprising said zeolite IZM-2 as described in patent application FR 2 984 911A, said process making it possible to improve the selectivity towards the production of middle distillate bases by limiting the production of light cracked products that cannot be incorporated into a gas oil and/or kerosene pool.

FR 2 918 050 B discloses an IZM-2 solid having an overall silicon to aluminium Si/Al mole ratio between 1 and infinity, and preferably between 25 and 312. In the illustrative example of patent application FR 2 984 911 A, a single IZM-2 solid having an overall Si/Al mole ratio of 53 is used in the formulation of the catalyst. This overall Si/Al mole ratio is calculated from the X-ray fluorescence characterization results.

The research studies carried out by the applicant have led it to discover that, surprisingly, the use of a catalyst based on a zeolite IZM-2 having an optimized Si/Al mole ratio in a process for isomerization of a paraffinic feedstock makes it possible to improve the activity of the catalyst while at the same time preserving maximum selectivity towards isomerization.

In particular, the use of such a catalyst in the isomerization process according to the invention produces optimal catalytic performance qualities in terms of activity and selectivity. Such a catalyst is substantially more selective than a catalyst comprising a zeolite IZM-2, the Si/Al mole ratio of which is less than 25 and it is substantially more active than a catalyst comprising a zeolite IZM-2, the Si/Al mole ratio of which is greater than 55.

A subject of the present invention relates to a process for the isomerization of paraffinic feedstocks, preferably derived from hydrotreated plant and/or animal oils or from low-temperature Fischer-Trospch synthesis, said process using a bifunctional catalyst comprising at least one metal of group VIII of the periodic table of elements, at least one matrix and at least one zeolite IZM-2, in which the ratio between the number of moles of silicon and number of moles of aluminium of the zeolite IZM-2 network is between 25 and 55.

SUBJECT OF THE INVENTION

The present invention relates to a process for the isomerization of paraffinic feedstocks operating at a temperature of between 200° C. and 500° C., at a total pressure between 0.45 MPa and 7 MPa, at a hydrogen partial pressure of between 0.3 and 5.5 MPa, at an hourly space velocity of between 0.1 and 10 kilograms of feedstock introduced per kilogram of catalyst and using a catalyst comprising at least one metal of group VIII of the periodic table of elements, at least one matrix and at least one zeolite IZM-2, in which the ratio between the number of moles of silicon and the number of moles of aluminium of the zeolite IZM-2 network is between 25 and 55.

For the purposes of the present invention, the expression "ratio between the number of moles of silicon and the number of moles of aluminium of zeolite IZM-2" is intended to mean the number of moles of silicon divided by the number of moles of aluminium of the zeolite IZM-2 network. The aluminium atoms present in the solid but not integrated into the framework of the zeolite (extra-network aluminium) are not therefore taken into account in the calculation.

One advantage of the present invention is that of providing a process for the isomerization of a paraffin feedstock using a catalyst based on a zeolite IZM-2 having an optimized Si/Al mole ratio making it possible to improve the activity of the catalyst while at the same time preserving maximum selectivity towards isomerization.

DETAILED DESCRIPTION OF THE INVENTION

In accordance with the invention, the present invention relates to a process for the isomerization of paraffinic feedstocks operating at a temperature of between 200° C. and 500° C., at a total pressure of between 0.45 MPa and 7 MPa, at a hydrogen partial pressure of between 0.3 and 5.5 MPa, at an hourly space velocity of between 0.1 and 10 kilograms of feedstock introduced per kilogram of catalyst and per hour and using a catalyst comprising at least one metal of group VIII of the periodic table of elements, at least one matrix and at least one zeolite IZM-2, in which the ratio between the number of moles of silicon and the number of moles of aluminium of the zeolite IZM-2 network is between 25 and 55, preferably between 25 and 50, and preferably between 30 and 50.

The Isomerization Process

In accordance with the invention, the isomerization process is carried out at a temperature of between 200° C. and 500° C., at a total pressure between 0.45 MPa and 7 MPa, at a hydrogen partial pressure of between 0.3 and 5.5 MPa, at an hourly space velocity of between 0.1 and 10 kilograms of feedstock introduced per kilogram of catalyst and per hour. Preferably, said process is carried out at a temperature of between 200 and 450° C., and more preferably between 220 and 430° C., at a total pressure of between 0.6 and 6 MPa, at a hydrogen partial pressure of between 0.4 and 4.8 MPa, at an hourly space velocity advantageously of between 0.2 and 7 $h^{-1}$ and preferably between 0.5 and 5 $h^{-1}$.

According to the invention, the isomerization process comprises bringing a paraffinic feedstock into contact with at least said catalyst according to the invention present in a catalytic reactor.

The paraffins of said paraffinic feedstock contain between 9 and 25 carbon atoms, preferably between 10 and 25 and very preferably between 10 and 22. The paraffin content in said feedstock used in the process according to the invention is advantageously greater than 90% by weight, preferably greater than 95% by weight and even more preferably greater than 98% by weight. Within said paraffins, the mass percentage of isoparaffins is less than 15%, preferably less than 10% and very preferably less than 5%.

According to a first embodiment, said paraffinic feedstock used in the process according to the invention is produced from renewable resources.

Preferably, said paraffinic feedstock is produced from renewable resources chosen from plant oils, oils from algae or algal oils, fish oils and fats of plant or animal origin, or mixtures of such feedstocks.

Said plant oils may advantageously be totally or partly raw or refined, and derived from plants chosen from rapeseed, sunflower, soybean, palm, olive, coconut, coconut kernel, castor oil plant, cotton, groundnut oil, linseed oil and sea kale oil, and all oils derived, for example, from sunflower or from rapeseed by genetic modification or hybridization, this list not being limiting. Said animal fats are advantageously chosen from blubber and fats composed of residues from the food industry or derived from the catering industries. Frying oils, various animal oils such as fish oils, tallow and lard may also be used.

The renewable resources from which is produced the paraffinic feedstock used in the process according to the invention essentially contain chemical structures of triglyceride type which those skilled in the art also know by the name fatty acid triester, and also free fatty acids, the fatty chains of which contain between 9 and 25 carbon atoms.

The hydrocarbon chain structure and length of these fatty acids is compatible with the hydrocarbons present in gas oil and kerosene, i.e. the middle distillate fraction. A fatty acid triester is thus composed of three fatty acid chains. These fatty acid chains in triester form or in free fatty acid form have a number of unsaturations per chain, also known as the number of carbon-carbon double bonds per chain, generally between 0 and 3, but which may be higher in particular for oils derived from algae which generally have from 5 to 6 unsaturations per chain.

The molecules present in said renewable resources used in the present invention thus have a number of unsaturations, expressed per triglyceride molecule, advantageously between 0 and 18. In these feedstocks, the degree of unsaturation, expressed as the number of unsaturations per hydrocarbon fatty chain, is advantageously between 0 and 6.

The renewable resources generally also include various impurities and especially heteroatoms such as nitrogen. The nitrogen contents in plant oils are generally between 1 ppm and 100 ppm by weight approximately, depending on their nature. They may be up to 1% by weight for particular feedstocks.

Said paraffinic feedstock used in the process according to the invention is advantageously produced from renewable resources according to processes known to those skilled in the art. One possible method is catalytic transformation of said renewable resources into deoxygenated paraffinic effluent in the presence of hydrogen, and in particular hydrotreatment.

Preferably, said paraffinic feedstock is produced by hydrotreatment of said renewable resources. These processes for the hydrotreatment of renewable resources are already well known and are described in numerous patents. By way of example, said paraffinic feedstock used in the process according to the invention may advantageously be produced, preferably by hydrotreatment and then by gas/liquid separation, from said renewable resources as, for example, in patent FR 2 910 483 or in patent FR 2 950 895.

According to a second embodiment, said paraffinic feedstock used in the process according to the invention may also be a paraffinic feedstock produced via a process involving a step of upgrading via the Fischer-Tropsch route. In the Fischer-Tropsch process, synthesis gas ($CO+H_2$) is converted catalytically into oxygenated products and into essentially linear hydrocarbons in gaseous, liquid or solid form. Said products obtained constitute the feedstock of the process according to the invention. Synthesis gas ($CO+H_2$) is advantageously produced from natural gas, coal, biomass, any source of hydrocarbon-based compounds or a mixture of these sources. Thus, the paraffinic feedstocks obtained, according to a Fischer-Tropsch synthetic process, from a synthesis gas ($CO+H_2$) produced from renewable resources, natural gas or coal may be used in the process according to the invention. Preferably, said paraffinic feedstock produced by Fischer-Tropsch synthesis and used in the process according to the invention predominantly comprises n-paraffins. Thus, said feedstock comprises a content of n-paraffins of greater than 60% by weight relative to the total mass of said feedstock. Said feedstock may also comprise a content of oxygenated products preferably of less than 10% by weight, a content of unsaturated substances, that is to say preferably olefinic products, preferably of less than 20% by weight, and a content of isoparaffins preferably of less than 10% by weight relative to the total mass of said feedstock.

Very preferably, said feedstock comprises a content of n-paraffins of greater than 70% by weight and even more preferably greater than 80% by weight relative to the total mass of said feedstock. The paraffins of said paraffinic feedstock contain between 9 and 25 carbon atoms, preferably between 10 and 25 and very preferably between 10 and 22.

Preferably, said paraffinic feedstock produced by Fischer-Tropsch synthesis is free of heteroatomic impurities, for instance sulfur, nitrogen or metals.

Catalyst

In accordance with the invention, the catalyst used in said process comprises at least one metal of group VIII of the periodic table of elements, at least one matrix and at least one zeolite IZM-2 in which the ratio between the number of moles of silicon and the number of moles of aluminium of the zeolite IZM-2 network is between 25 and 55, preferably between 25 and 50 and preferably between 30 and 50.

Zeolite IZM-2

In accordance with the invention, the catalyst comprises zeolite IZM-2. Zeolite IZM-2 is a crystalline microporous solid having a crystalline structure described in patent application FR 2 918 050. Zeolite IZM-2 has an X-ray diffraction pattern which includes at least the lines recorded in Table 1.

Advantageously, the diffraction pattern is obtained by radiocrystallographic analysis by means of a diffractometer using the conventional powder method with $K_{\alpha 1}$ radiation of copper ($\lambda$=1.5406 Å). On the basis of the position of the diffraction peaks represented by the angle $2\theta$, the lattice constant distances $d_{hkl}$ characteristic of the sample are calculated using the Bragg relationship. The measurement error $\Delta(d_{hkl})$ on $d_{hkl}$ is calculated by virtue of the Bragg relationship as a function of the absolute error $\Delta(2\theta)$ assigned to the measurement of $2\theta$. An absolute error $\Delta(2\theta)$ equal to $\pm 0.02°$ is commonly accepted. The relative intensity $I_{rel}$ assigned to each value of $d_{hkl}$ is measured according to the height of the corresponding diffraction peak. The X-ray pattern of IZM-2 according to the invention comprises at least the lines at the values of $d_{hkl}$ given in Table 1. In the column of the $d_{hkl}$ values, the mean values of the inter-lattice distances in Angströms (Å) are given. Each of these values must be assigned the measurement error $\Delta(d_{hkl})$ between $\pm 0.6$ Å and $\pm 0.01$ Å.

TABLE 1 mean values of $d_{hkl}$ and relative intensities measured on an X-ray diffraction pattern of the calcined IZM-2 crystalline solid

| 2 theta (°) | $d_{hkl}$ (Å) | $I_{rel}$ | 2 theta (°) | $d_{hkl}$ (Å) | $I_{rel}$ |
|---|---|---|---|---|---|
| 5.07 | 17.43 | vw | 19.01 | 4.66 | vw |
| 7.36 | 12.01 | VS | 19.52 | 4.54 | vw |
| 7.67 | 11.52 | VS | 21.29 | 4.17 | m |
| 8.78 | 10.07 | S | 22.44 | 3.96 | w |
| 10.02 | 8.82 | vw | 23.10 | 3.85 | mw |
| 12.13 | 7.29 | vw | 23.57 | 3.77 | w |
| 14.76 | 6.00 | vw | 24.65 | 3.61 | vw |
| 15.31 | 5.78 | vw | 26.78 | 3.33 | w |
| 15.62 | 5.67 | vw | 29.33 | 3.04 | vw |
| 16.03 | 5.52 | vw | 33.06 | 2.71 | vw |
| 17.60 | 5.03 | vw | 36.82 | 2.44 | vw |
| 18.22 | 4.87 | vw | 44.54 | 2.03 | vw | where VS = very strong;
S = strong;
m = medium;
mw = moderately weak;
w = weak;
vw = very weak The relative intensity $I_{rel}$ is given in relation to a relative intensity scale in which a value of 100 is arbitrarily assigned to the most intense line in the X-ray diffraction pattern: vw<15; 15≤30; 30<mw<50; 50≤m<65; 65≤S<85; VS≥85.

IZM-2 has a chemical composition, expressed on an anhydrous basis, in terms of moles of oxides, defined by the following general formula: SiO$_2$: a Al$_2$O$_3$: b M$_{2/n}$O, in which M is at least one alkali metal and/or one alkaline-earth metal having a valency n. In said formula given above, a represents the number of moles of Al$_2$O$_3$ and b represents the number of moles of M$_{2/n}$O.

In accordance with the invention, said catalyst used in said process comprises at least one zeolite IZM-2 in which the ratio between the number of moles of silicon and the number of moles of aluminium of the zeolite IZM-2 network is between 25 and 55, preferably between 25 and 50 and preferably between 30 and 50.

According to the invention, the ratio of the number of moles of silicon divided by the number of moles of aluminium of the zeolite IZM-2 network (Si/Al) is calculated according to the formula:

$$Si/Al = n_{Si}/n_{Al}$$

with:

$n_{Si}/n_{Al}$: ratio of the number of moles of silicon divided by the number of moles of network aluminium, in mole/mole, $n_{Si}$: moles of silicon per gram of zeolite, in moles/gram, $n_{Al}$: moles of network aluminium per gram of zeolite, in moles/gram.

According to the invention, the number of moles of network aluminium per gram of zeolite IZM-2 is determined from the weight (wt) percentage (%) of aluminium of the zeolite and the percentage of tetracoordinated and pentacoordinated aluminium present in the zeolite according to the formula:

$$n_{Al} = [(wt \% Al) \times (\% NMRAl^{IV} + \% NMRAl^{V})]/[MM(Al) \times 10\,000]$$

with:

$n_{Al}$: moles of network aluminium per gram of zeolite, in moles/gram, wt % Al: weight percentage of aluminium in the zeolite (dry mass), measured by inductively coupled plasma (ICP) on a Spectro Arcos ICP-OES instrument from SPECTRO according to the ASTM D7260 method, MM(Al): molar mass of the aluminium, in gram/mole, % NMRAl$^{IV}$: weight percentage of tetracoordinated aluminium in the zeolite, measured by nuclear magnetic resonance of $^{27}$Al, % NMRAl$^{V}$: weight percentage of the pentacoordinated aluminium in the zeolite, measured by nuclear magnetic resonance of $^{27}$Al.

The tetracoordinated and pentacoordinated aluminium atoms are considered to be network aluminiums, that is to say to be aluminiums integrated into the framework of the zeolite.

The weight percentage of the tetracoordinated and pentacoordinated aluminium atoms present in zeolite IZM-2 is determined by nuclear magnetic resonance of the solid of $^{27}$Al. Aluminium NMR is in fact known to be used with a view to pinpointing and quantifying the various coordination states of this nucleus ("Analyse physico-chimiques des catalyseurs industriels" ["Physicochemical analysis of industrial catalysts"], J. Lynch, Editions Technip (2001) chap. 13, pages 290 and 291). The NMR spectrum of the aluminium of zeolite IZM-2 can exhibit three signals, a first being characteristic of the resonance of the tetracoordinated aluminium atoms, a second being characteristic of the pentacoordinated aluminium atoms and a third being characteristic of the resonance of the hexacoordinated aluminium atoms. The hexacoordinated aluminium atoms are considered to be extra-network aluminiums.

The tetracoordinated aluminium atoms (denoted Al$^{IV}$) resonate at a chemical shift typically of between +50 ppm and +70 ppm, the pentacoordinated aluminium atoms (denoted Al$^V$) resonate at a chemical shift typically of between +20 ppm and +40 ppm and the hexacoordinated aluminium atoms (denoted Al$^{VI}$) resonate at a chemical shift typically of between −20 ppm and +10 ppm. The weight percentage of the various aluminium species is quantified from the integration of the signals corresponding to each of these species.

More specifically, the zeolite IZM-2 present in the catalyst according to the invention was analysed by MAS-NMR of the solid $^{27}$Al on an Avance Brücker 400 MHz spectrometer using a 4 mm probe optimized for $^{27}$Al. The spin speed of the sample is about 12 kHz. The aluminium atom is a quadrupolar nucleus, the spin of which is equal to 5/2. Under "selective" analysis conditions, namely a field of low radiofrequency equal to 30 kHz, a small pulse angle equal to π/2 and in the presence of a sample saturated with water, the magic-angle spinning (MAS) NMR technique, denoted MAS-NMR, is a quantitative technique. The decomposition of each MAS-NMR makes it possible to directly obtain the amount of the various aluminium species, namely of the tetracoordinated Al$^{IV}$, pentacoordinated Al$^V$ and hexacoordinated Al$^{VI}$ aluminium atoms. Each spectrum is tuned with respect to chemical shift relative to a molar solution of aluminium nitrate for which the aluminium signal is at zero ppm. The signals characterizing the tetracoordinated aluminium atoms Al$^{IV}$ are typically integrated between +50 ppm and +70 ppm, which corresponds to the area 1, the signals characterizing the pentacoordinated aluminium atoms Al$^V$ are typically integrated between +20 ppm and +40 ppm, which corresponds to the area 2, and the signals characterizing the hexacoordinated aluminium atoms Al$^{VI}$ are typically integrated between −20 ppm and +10 ppm, which corresponds to the area 3. The weight percentage of each aluminium species is calculated from the ratio of its area to the total area. For example, the weight percentage of hexacoordinated aluminium atoms Al$^{VI}$ (denoted % NMRAl$^{VI}$) is calculated as follows:

$$\% NMRAl^{VI} = (area\ 3) \times 100/(area\ 1 + area\ 2 + area\ 3)$$

Advantageously, zeolite IZM-2 according to the invention has a weight percentage of hexacoordinated aluminium atoms Al$^{VI}$ (denoted % NMRAl$^{VI}$) of less than 50%, preferably less than 40%, and very preferably less than 30%.

The number of moles of silicon per gram of zeolite IZM-2 is determined from the weight (wt) percentage (%) of silicon of the zeolite according to the formula:

$$n_{Si} = [(wt \% Si)/[MM(Si) \times 100]$$

with:

$n_{Si}$: moles of silicon per gram of zeolite, in moles/gram, wt % Si: weight percentage of aluminium in the zeolite (dry mass), measured by X-ray fluorescence with sample discs on an Axios instrument, of the PANalytical brand working at 125 mA and 32 kV, MM(Si): molar mass of the silicon, in grams/mole.

The Si/Al mole ratio desired according to the invention for zeolite IZM-2 can be obtained directly during the zeolite synthesis step by adjusting the synthesis conditions and in particular the composition of the synthesis gel by controlling for example the relative amounts of silicon and aluminium used in the synthesis gel.

A process for preparing zeolite IZM-2 is taught in application FR 2 918 050 A.

Advantageously, an aqueous mixture comprising at least one source of at least one oxide $SiO_2$, optionally at least one source of at least one oxide $Al_2O_3$, optionally at least one source of at least one alkali metal and/or alkaline-earth metal with a valency n, and preferably at least one organic species R comprising two quaternary nitrogen atoms, is reacted, the mixture preferentially having the following molar composition:

$SiO_2/Al_2O_3$: at least 2, preferably at least 20, more preferably from 60 to 600, $H_2O/SiO_2$: 1 to 100, preferably from 10 to 70, $R/SiO_2$: 0.02 to 2, preferably from 0.05 to 0.5, $M_{2/n}O/SiO_2$: 0 to 1, preferably from 0.005 to 0.5, where M is one or more alkali metals and/or alkaline-earth metals chosen from lithium, sodium, potassium, calcium and magnesium, and the mixture of at least two of these metals, preferably M is sodium. Advantageously, the element R is 1,6-bis(methylpiperidinium)hexane.

In accordance with the invention, the Si/Al mole ratio of zeolite IZM-2 can also be adjusted to the desired value by methods of post-treatment of zeolite IZM-2 obtained after synthesis. Such methods are known to those skilled in the art and make it possible to carry out dealumination or desilication of the zeolite. Preferably, the Si/Al mole ratio of zeolite IZM-2 which is part of the composition of the catalyst according to the invention is adjusted by means of a suitable choice of the conditions for synthesis of said zeolite.

The zeolite IZM-2 present in the catalyst according to the invention is very advantageously in its acid form, that is to say in protonated form $H^+$. In such a case, it is advantageous for the ratio of the number of moles of cation other than the proton per gram of zeolite IZM-2, divided by the number of moles of network aluminium per gram of zeolite IZM-2, to be less than 0.9, preferably less than 0.6 and very preferably less than 0.3. To do this, the zeolite IZM-2 participating in the composition of the catalyst according to the invention can for example be exchanged via at least one treatment with a solution of at least one ammonium salt so as to obtain the ammonium form of the zeolite IZM-2, which, once calcined, results in the acid form of said zeolite IZM-2. This exchange step may be performed at any step in the preparation of the catalyst, i.e. after the step of preparing zeolite IZM-2, after the step of forming zeolite IZM-2 with a matrix, or even after the step of introducing the hydro-dehydrogenating metal. Preferably, the exchange step is carried out after the step of shaping the zeolite IZM-2.

Matrix

In accordance with the invention, said catalyst prepared comprises at least one matrix. Said matrix may advantageously be amorphous or crystalline.

Preferably, said matrix is advantageously chosen from the group formed by alumina, silica, silica-alumina, clays, titanium oxide, boron oxide and zirconia, taken alone or as a mixture, or else aluminates may also be chosen. Preferably, alumina is used as matrix. Preferably, said matrix contains alumina in all its forms known to those skilled in the art, for instance aluminas of alpha, gamma, eta and delta type. Said aluminas differ in their specific surface and their pore volume. The mixture of the matrix and of the zeolite IZM-2 formed constitutes the support for the catalyst.

Metal Phase

In accordance with the invention, the catalyst comprises at least one metal of group VIII preferably chosen from iron, cobalt, nickel, ruthenium, rhodium, palladium, osmium, iridium and platinum, preferably chosen from the noble metals of group VIII, very preferably chosen from palladium and platinum and even more preferably platinum is chosen.

Preferably, said catalyst comprises a content of metal of group VIII of between 0.01% and 5% by weight relative to the total weight of said catalyst and preferably of between 0.1% and 4% by weight.

In the case where said catalyst comprises at least one noble metal of group VIII, the content of noble metal of said catalyst is advantageously between 0.01% and 5% by weight, preferably between 0.1% and 4% by weight and very preferably between 0.1% and 2% by weight relative to the total weight of said catalyst.

The catalyst of the invention may also advantageously contain at least one metal chosen from the metals of groups IIIA, IVA and VIIB chosen from gallium, indium, tin and rhenium. In this case, the content of metal chosen from the metals of groups IIIA, IVA and VIIB is preferably between 0.01% and 2%, preferably between 0.05% and 1% by weight relative to the total weight of said catalyst.

The dispersion of the metal(s) of group VIII, determined by chemisorption, for example by $H_2/O_2$ titration or by carbon monoxide chemisorption, is between 10% and 100%, preferably between 20% and 100% and more preferably between 30% and 100%. The macroscopic distribution coefficient for the metal(s) of group VIII, obtained from its (their) profile determined with a Castaing microprobe, defined as the ratio of the concentrations of the metal(s) of group VIII at the core of the grain relative to at the edge of this same grain, is between 0.7 and 1.3 and preferably between 0.8 and 1.2. The value of this ratio, in the region of 1, is evidence of the homogeneity of distribution of the metal(s) of group VIII in the catalyst.

Said catalyst may advantageously comprise at least one additional metal chosen from the group formed by metals of groups IIIA, IVA and VIIB of the periodic table of elements, preferably chosen from gallium, indium, tin and rhenium. Said additional metal is preferably chosen from indium, tin and rhenium.

Preparation of the Catalyst

The catalyst according to the invention may advantageously be prepared according to any of the methods well known to those skilled in the art.

Forming

Advantageously, the various constituents of the support of the catalyst can be formed by means of a blending step so as to form a paste, then extrusion of the paste obtained, or else by mixing powders then pelletizing, or else by any other known process for agglomeration of a powder containing alumina. The supports thus obtained may be in various shapes and sizes. Preferably, the forming is carried out by blending and extrusion.

During the forming of the support by blending and then extrusion, said zeolite IZM-2 may be introduced during the dissolution or suspension of the alumina compounds or alumina precursors, for instance boehmite. Said zeolite IZM-2 may be, for example, without this being limiting, in the form of a powder, a ground powder, a suspension, or a suspension which has undergone a deagglomeration treatment. Thus, for example, said zeolite may advantageously be placed in acidified or non-acidified suspension at a concentration adjusted to the final IZM-2 content targeted in the catalyst according to the invention. This suspension commonly referred to as a slip is then mixed with the alumina compounds or alumina precursors.

Moreover, the use of additives may advantageously be performed to facilitate the forming and/or to improve the final mechanical properties of the supports, as is well known to those skilled in the art. Examples of additives that may especially be mentioned include cellulose, carboxymethylcellulose, carboxyethylcellulose, tall oil, xanthan gums, surfactants, flocculants such as polyacrylamides, carbon black, starches, stearic acid, polyacryl alcohol, polyvinyl alcohol, biopolymers, glucose, polyethylene glycols, etc.

Water may advantageously be added or removed to adjust the viscosity of the paste to be extruded. This step may advantageously be performed at any stage in the blending step.

To adjust the solids content of the paste to be extruded so as to make it extrudable, a compound that is predominantly solid, preferably an oxide or a hydrate, may also be added. A hydrate is preferably used, and even more preferably an aluminium hydrate. The loss on ignition of this hydrate is advantageously greater than 15%.

Extrusion of the paste derived from the blending step may advantageously be performed with any conventional commercially available tool. The paste resulting from the kneading is advantageously extruded through a die, for example using a piston, a single extruding screw or twin extruding screws. The extrusion may advantageously be performed via any method known to those skilled in the art.

The catalyst supports according to the invention are generally in the form of cylindrical extrudates or polylobal extrudates such as bilobal, trilobal or polylobal extrudates of straight or twisted form, but may optionally be manufactured and used in the form of crushed powders, lozenges, rings, beads and/or wheels. Preferably, the catalyst supports according to the invention are in the form of spheres or extrudates. Advantageously, the support is in the form of extrudates with a diameter of between 0.5 and 5 mm and more particularly between 0.7 and 2.5 mm. The forms may be cylindrical (which may or may not be hollow) and/or twisted and/or multilobal (for example 2, 3, 4 or 5 lobes) cylindrical and/or annular. The multilobal form is advantageously preferably used.

Drying

The support thus obtained can then be subjected to a drying step. Said drying step is advantageously performed via any technique known to those skilled in the art.

Preferably, the drying is carried out under a stream of air. Said drying may also be performed under a flow of any oxidizing, reducing or inert gas. Preferably, the drying is advantageously performed at a temperature of between 50 and 180° C., preferably between 60 and 150° C. and very preferably between 80 and 130° C.

Calcination

Said support, optionally dried, then preferably undergoes a calcination step.

Said calcination step is advantageously carried out in the presence of molecular oxygen, for example by flushing with air, at a temperature advantageously of greater than 200° C. and less than or equal to 1100° C. Said calcination step can advantageously be carried out in a traversed bed, in a swept bed or under a static atmosphere. For example, the oven used can be a rotary oven or can be a vertical oven comprising radial traversed layers. Preferably, said calcination step is carried out for between more than one hour at 200° C. and less than one hour at 1100° C. The calcination can advantageously be carried out in the presence of steam and/or in the presence of an acidic or basic vapour. For example, the calcination can be carried out under a partial pressure of ammonia.

Post-Calcination Treatments

Post-calcination treatments may optionally be performed, so as to improve the properties of the support, especially the textural properties.

Thus, the catalyst support used in the process according to the present invention may be subjected to a hydrothermal treatment in a confined atmosphere. The term "hydrothermal treatment in a confined atmosphere" means a treatment in an autoclave in the presence of water at a temperature above ambient temperature, preferably above 25° C., preferably above 30° C.

In the course of this hydrothermal treatment, the support may advantageously be impregnated, prior to its treatment in the autoclave (the autoclaving being done either in the vapour phase or in the liquid phase, this vapour or liquid phase of the autoclave possibly being acidic or not). This impregnation, prior to the autoclaving, can advantageously be acidic or non-acidic. This impregnation, prior to the autoclaving, can advantageously be carried out dry or by immersion of the support in an acidic aqueous solution. The term "dry impregnation" is understood to mean bringing the support into contact with a volume of solution less than or equal to the total pore volume of the support. Preferably, the impregnation is performed dry. The autoclave is preferably a rotating-basket autoclave such as the one defined in patent application EP 0 387 109 A. The temperature during the autoclaving may be between 100 and 250° C. for a period of time of between 30 minutes and 3 hours.

Deposition of the Metal Phase

For the deposition of the metal of group VIII of the periodic table of elements, all the deposition techniques known to those skilled in the art and all the precursors of such metals may be suitable. Use may be made of the deposition techniques by dry impregnation or excess impregnation of a solution containing the precursors of the metals, in the presence or absence of competitors. The introduction of the metal can be carried out at any step of the preparation of the catalyst: on zeolite IZM-2 and/or on the matrix, in particular before the forming step, during the forming step, or after the forming step, on the support of the catalyst. Preferably, the deposition of the metal is performed after the forming step.

The control of certain parameters used during the deposition, in particular the nature of the precursor of the metal(s) of group VIII used, makes it possible to direct the deposition of said metal(s) predominantly on the matrix or on the zeolite.

Thus, to introduce the metal(s) of group VIII, preferentially platinum and/or palladium, predominantly on the matrix, an anionic exchange can be carried out with hexachloroplatinic acid and/or hexachlorpalladic acid, in the presence of a competing agent, for example hydrochloric acid, the deposition being in general followed by a calcination, for example at a temperature of between 350 and 550° C., and for a period of between 1 and 4 hours. With such precursors, the metal(s) of group VIII is (are) deposited predominantly on the matrix and said metal(s) exhibit(s) a good dispersion and a good macroscopic distribution through the catalyst grain.

It is also possible to envisage depositing the metal(s) of group VIII, preferentially platinum and/or palladium, by cationic exchange such that said metal(s) is (are) predominantly on the zeolite. Thus, in the case of platinum, the precursor can for example be chosen from:

ammoniacal compounds such as platinum(II) tetramine salts of formula $Pt(NH_3)_4X_2$; platinum(IV) hexamine salts of formula $Pt(NH_3)_6X_4$; platinum(IV) halopentamine salts of formula $(PtX(NH_3)_5)X_3$; platinum N-tetahalodiamine salts of formula $PtX_4(NH_3)_2$; and halogenated compounds of formula $H(Pt(acac)_2X)$;

X being a halogen chosen from the group made up of chlorine, fluorine, bromine and iodine, X preferably being chlorine, and "acac" representing the acetylacetonate group (of empirical formula $C_5H_7O_2$), derived from acetylacetone. With such precursors, the metal(s) of group VIII is (are) deposited predominantly on the zeolite and said metal(s) exhibit(s) a good dispersion and a good macroscopic distribution through the catalyst grain.

In the case where the catalyst of the invention also contains at least one metal chosen from the metals of groups IIIA, IVA and VIIB, all the techniques for deposition of such a metal that are known to those skilled in the art and all the precursors of such metals may be suitable.

The metal(s) of group VIII and that (those) of groups IIIA, IVA and VIIB can be added either separately or simultaneously in at least one unit step. When at least one metal of groups IIIA, IVA and VIIB is added separately, it is preferable for it to be added after the metal of group VIII.

The additional metal chosen from the metals of groups IIIA, IVA and VIIB may be introduced by means of compounds such as, for example, chlorides, bromides and nitrates of the metals of groups IIIA, IVA and VIIB. For example, in the case of indium, the nitrate or the chloride is advantageously used, and, in the case of rhenium, perrhenic acid is advantageously used. The additional metal chosen from the metals of groups IIIA, IVA and VIIB may also be introduced in the form of at least one organic compound chosen from the group consisting of complexes of said metal, in particular polyketone complexes of the metal and hydrocarbylmetals such as alkyl, cycloalkyl, aryl, alkylaryl and arylalkyl metals. In the latter case, the introduction of the metal is advantageously performed using a solution of the organometallic compound of said metal in an organic solvent. Organohalogen compounds of the metal may also be used. Organic compounds of metals that may be mentioned in particular include tetrabutyltin, in the case of tin, and triphenylindium, in the case of indium.

If the additional metal chosen from the metals of groups IIIA, IVA and VIIB is introduced before the metal of group VIII, the compound of the IIIA, IVA and/or VIIB metal used is generally chosen from the group constituted by the halide, nitrate, acetate, tartrate, carbonate and oxalate of the metal. The introduction is then advantageously performed in an aqueous solution. However, it may also be introduced using a solution of an organometallic compound of the metal, for example tetrabutyltin. In this case, before introducing at least one metal of group VIII, calcination in air will be performed.

Furthermore, intermediate treatments, for instance calcination and/or reduction, may be applied between the successive depositions of the various metals.

Before its use in the process according to the invention, the catalyst is preferably reduced. This reduction step is advantageously performed by treatment under hydrogen at a temperature of between 150° C. and 650° C. at a total pressure of between 0.1 and 25 MPa. For example, a reduction consists of a stationary phase at 150° C. for two hours and then a temperature increase up to 450° C. at a rate of 1° C./minute, and then a stationary phase of two hours at 450° C.; throughout this reduction step, the hydrogen flow rate is 1000 normal m³ of hydrogen per tonne of catalyst and the total pressure is kept constant at 0.2 MPa. Any ex situ reduction method can advantageously be envisaged. Prior reduction of the final catalyst ex-situ, under a stream of hydrogen, may be performed, for example at a temperature of from 450° C. to 600° C., for a time of from 0.5 to 4 hours.

Said catalyst also advantageously comprises sulfur. In the case where the catalyst of the invention contains sulfur, said sulfur may be introduced at any step in the preparation of the catalyst: before or after the forming and/or drying and/or calcination step, before and/or after the introduction of the metal(s) mentioned previously, or alternatively by in-situ and/or ex-situ sulfurization before the catalytic reaction. In the case of in-situ sulfurization, the reduction, if the catalyst has not been reduced beforehand, takes place before the sulfurization. In the case of ex-situ sulfurization, the reduction is also performed, followed by sulfurization. The sulfurization is preferably performed in the presence of hydrogen using any sulfurizing agent that is well known to those skilled in the art, for instance dimethyl sulfide or hydrogen sulfide.

The catalysts according to the invention are in various shapes and sizes. They are generally used in the form of cylindrical extrudates and/or polylobal extrudates such as bilobal, trilobal or polylobal extrudates of straight and/or twisted form, but may optionally be manufactured and used in the form of crushed powders, lozenges, rings, beads and/or wheels. Preferably, the catalysts employed in the process according to the invention are in the form of spheres or of extrudates. Advantageously, the catalyst is in the form of extrudates with a diameter of between 0.5 and 5 mm and more particularly between 0.7 and 2.5 mm. The forms may be cylindrical (which may or may not be hollow) and/or twisted and/or multilobal (for example 2, 3, 4 or 5 lobes) cylindrical and/or annular. The multilobal form is advantageously preferably used. The metal deposit does not change the form of the support.

Said catalyst according to the invention more particularly comprises, and preferably consists of:
- from 1% to 90%, preferably from 3% to 80% and more preferably from 4% to 60% and even more preferably from 6% to 50% by weight of zeolite IZM-2 according to the invention,
- from 0.01% to 5% by weight, preferably between 0.1% and 4% by weight and very preferably between 0.1% and 2% by weight of at least one metal of group VIII of the periodic table of elements, preferably platinum,
- optionally from 0.01% to 2% and preferably from 0.05% to 1% by weight of at least one additional metal chosen from the group formed by metals of groups IIIA, IVA and VIIB,
- optionally a sulfur content, preferably such that the ratio of the number of moles of sulfur to the number of moles of the metal(s) of group VIII is between 0.3 and 3,
- at least one matrix, preferably alumina, providing the remainder to 100% in the catalyst.

The examples that follow illustrate the invention without, however, limiting its scope. Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 18/55.286, filed Jun. 15, 2018, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Example 1 (not in Accordance with the Invention): Preparation of the Catalyst A

Synthesis of Zeolite IZM-2

781 mg of a zeolite of structural type FAU (CBV720, Zeolyst) were mixed with 6076.6 mg of an aqueous solution of 1,6-bis(methylpiperidinium)hexane dibromide (20.04% by weight). 4203 mg of deionized water are added to the previous mixture, and the preparation obtained is kept stirring for 10 minutes. 548 mg of an aqueous solution containing 20% by weight of sodium hydroxide (90% by weight, Aldrich) are added. In order to promote the formation of the crystalline solid IZM-2, 103 mg of zeolite IZM-2 seeds are added to the synthesis mixture, and stirring is maintained for 15 minutes. Subsequently, 610.3 mg of colloidal silica (Ludox HS40, 40% by weight, Aldrich) were incorporated into the synthesis mixture, and said mixture was kept stirring for the amount of time required to evaporate off the solvent until the desired gel concentration was obtained, that is to say a molar composition of the following mixture: 1 $SiO_2$, 0.025 $Al_2O_3$, 0.17 1,6-bis(methylpiperidinium)hexane dibromide, 0.0835 $Na_2O$, 33.33 $H_2O$. The mixture is then transferred, after homogenization, into an autoclave. The autoclave is closed and then heated for 6 days at 170° C. with stirring. The crystalline product obtained is filtered off, washed with deionized water, then dried overnight at 100° C. The solid is then introduced into a muffle furnace where a calcination step is carried out: the calcination cycle comprises an increase in temperature up to 200° C., a stationary phase at 200° C. maintained for 2 hours, an increase in temperature up to 550° C., followed by a stationary phase at 550° C. maintained for 8 hours, then a return to ambient temperature. The synthesis is reproduced several times in order to have a sufficient amount of solid for the characterizations and the subsequent preparation steps. The solid thus obtained is then refluxed for 2 hours in an aqueous ammonium nitrate solution (10 ml of solution per gram of solid, ammonium nitrate concentration of 3M) so as to exchange the sodium alkaline cations with ammonium ions. This refluxing step is performed four times, and the solid is then filtered off, washed with deionized water and dried in an oven overnight at 100° C. Finally, to obtain the zeolite in its proton (acid) form, a step of calcination is performed at 550° C. for 10 hours (temperature increase gradient of 5° C./minute) in a traversed bed under dry air (2 standard litres per hour and per gram of solid). The solid thus obtained was analysed by x-ray diffraction and identified as being constituted by zeolite IZM-2. Characterizations by $I^{27}Al$ NMR, X-ray fluorescence and atomic absorption make it possible to obtain the following results for IZM-2:

weight percentage of hexacoordinated aluminium atoms $Al^{VI}$: 8%, ratio of the number of moles of silicon divided by the number of moles of network aluminium, in mol/mol, Si/Al: 22 ratio of the number of moles of sodium divided by the number of moles of network aluminium, in mol/mol, Si/Al: 0.02.

Preparation of the IZM-2/Alumina Support

The IZM-2/alumina support is obtained by blending and extrusion of the zeolite IZM-2 with a GA7001 alumina gel provided by the company Axens. The blended paste is extruded through a trilobal die 1.8 mm in diameter. After drying in an oven overnight at 110° C., the extrudates are calcined at 500° C. for two hours (temperature increase rate of 5° C./minute) in a traversed bed under dry air (2 standard litres per hour and per gram of solid). The weight content of zeolite IZM-2 on the support after calcination is 25% by weight.

Platinum Deposition

The platinum is deposited by excess impregnation of the IZM-2/alumina support with an aqueous solution containing hexachloroplatinic acid. The concentration of hexachloroplatinic acid in the solution is $2.55 \times 10^{-3}$ mol/l. 20 g of support are used, the pore volume of which is filled with distilled water and the solid is left to mature for one hour at ambient temperature. The solid is then immersed in 80 ml of a hydrochloric acid HCl solution of concentration $3.52 \times 10^{-1}$ mol/l in a conical flask, and the whole is then stirred on a stirring table (100 rpm) at ambient temperature for one hour. The hydrochloric acid solution is then removed and the solid is immersed in 80 ml of the hexachloroplatinic acid solution described previously, and the whole is then stirred on a stirring table (100 rpm) at ambient temperature for 24 hours. The impregnation solution is then removed and the solid is rinsed with 160 ml of distilled water. The solid is then dried in a ventilated oven overnight at 110° C. and, finally, a calcination step is performed under a flow of dry air (2 standard litres per hour and per gram of solid) in a tubular oven under the following conditions:

temperature increase from ambient temperature to 500° C. at 5° C./min;

stationary phase of two hours at 500° C.;

decrease to ambient temperature.

The Pt content measured by XRF on the calcined catalyst is 0.19% by weight, its dispersion measured by $H_2/O_2$ assay is 85%, and its coefficient of distribution measured by Castaing microprobe is 0.94.

Example 2 (in Accordance with the Invention): Preparation of the Catalyst B

Synthesis of Zeolite IZM-2

This zeolite IZM-2 was synthesized in accordance with the teaching of patent application FR 2 918 050. A colloidal silica suspension known under the trade name Ludox HS-40, sold by Aldrich, is incorporated into a solution composed of sodium hydroxide (Prolabo), 1,6-bis(methylpiperidinium) hexane dibromide structuring agent, aluminium hydroxide (Aldrich) and deionized water. The molar composition of the mixture is as follows: 1 $SiO_2$, 0.0166 $Al_2O_3$, 0.1666 $Na_2O$, 0.1666 1,6-bis(methylpiperidinium)hexane, 33.3333 $H_2O$. The mixture is stirred vigorously for half an hour. The mixture is then transferred, after homogenization, into a Parr autoclave. The autoclave is heated for 5 days at 170° C. with spindle stirring (30 rpm). The product obtained is filtered, washed with deionized water to reach neutral pH and then dried overnight at 100° C. in an oven. The solid is then introduced into a muffle furnace and calcined so as to remove the structuring agent. The calcination cycle comprises a temperature rise up to 200° C., a stationary phase of two hours at this temperature, a temperature rise up to 550°

C., followed by a stationary phase of eight hours at this temperature and finally a return to ambient temperature. The temperature rises are performed with a gradient of 2° C./minute. The solid thus obtained is then refluxed for 2 hours in an aqueous ammonium nitrate solution (10 ml of solution per gram of solid, ammonium nitrate concentration of 3M) so as to exchange the sodium alkaline cations with ammonium ions. This refluxing step is performed four times, and the solid is then filtered off, washed with deionized water and dried in an oven overnight at 100° C. Finally, to obtain the zeolite in its proton (acid) form, a step of calcination is performed at 550° C. for 10 hours (temperature increase gradient of 5° C./minute) in a traversed bed under dry air (2 standard litres per hour and per gram of solid). The solid thus obtained was analysed by X-ray diffraction and identified as being constituted by zeolite IZM-2. Characterizations by $I^{27}Al$ NMR, X-ray fluorescence and atomic absorption make it possible to obtain the following results for IZM-2:

weight percentage of hexacoordinated aluminium atoms $Al^{VI}$: 7%, ratio of the number of moles of silicon divided by the number of moles of network aluminium, in mol/mol, Si/Al: 32, ratio of the number of moles of sodium divided by the number of moles of network aluminium, in mol/mol, Si/Al: 0.07.

Preparation of the IZM-2/Alumina Support

The IZM-2/alumina support is obtained according to the same process as that described in Example 1.

Platinum Deposition

The platinum is deposited by excess impregnation of the IZM-2/alumina support according to the same process as that described in Example 1.

The Pt content measured by XRF on the calcined catalyst is 0.20% by weight, its dispersion measured by $H_2/O_2$ assay is 83%, and its coefficient of distribution measured by Castaing microprobe is 0.98.

Example 3 (in Accordance with the Invention): Preparation of the Catalyst C

Synthesis of Zeolite IZM-2

This zeolite IZM-2 was synthesized in accordance with the teaching of patent application FR 2 918 050. A colloidal silica suspension known under the trade name Ludox HS-40, sold by Aldrich, is incorporated into a solution composed of sodium hydroxide (Prolabo), 1,6-bis(methylpiperidinium) hexane dibromide structuring agent, aluminium hydroxide (Aldrich) and deionized water. The molar composition of the mixture is as follows: 1 $SiO_2$, 0.0100 $Al_2O_3$, 0.1666 $Na_2O$, 0.1666 1,6-bis(methylpiperidinium)hexane, 33.3333 $H_2O$. The mixture is stirred vigorously for half an hour. The mixture is then transferred, after homogenization, into a Parr autoclave. The autoclave is heated for 5 days at 170° C. with spindle stirring (30 rpm). The product obtained is filtered, washed with deionized water to reach neutral pH and then dried overnight at 100° C. in an oven. The solid is then introduced into a muffle furnace and calcined so as to remove the structuring agent. The calcination cycle comprises a temperature rise up to 200° C., a stationary phase of two hours at this temperature, a temperature rise up to 550° C., followed by a stationary phase of eight hours at this temperature and finally a return to ambient temperature. The temperature rises are performed with a gradient of 2° C./minute. The solid thus obtained is then refluxed for 2 hours in an aqueous ammonium nitrate solution (10 ml of solution per gram of solid, ammonium nitrate concentration of 3M) so as to exchange the sodium alkaline cations with ammonium ions. This refluxing step is performed four times, and the solid is then filtered off, washed with deionized water and dried in an oven overnight at 100° C. Finally, to obtain the zeolite in its proton (acid) form, a step of calcination is performed at 550° C. for 10 hours (temperature increase gradient of 5° C./minute) in a traversed bed under dry air (2 standard litres per hour and per gram of solid). The solid thus obtained was analysed by X-ray diffraction and identified as being constituted by zeolite IZM-2. Characterizations by $I^{27}Al$ NMR, X-ray fluorescence and atomic absorption make it possible to obtain the following results for IZM-2:

weight percentage of hexacoordinated aluminium atoms $Al^{VI}$: 6%, ratio of the number of moles of silicon divided by the number of moles of network aluminium, in mol/mol, Si/Al: 46, ratio of the number of moles of sodium divided by the number of moles of network aluminium, in mol/mol, Si/Al: 0.08.

Preparation of the IZM-2/Alumina Support

The IZM-2/alumina support is obtained according to the same process as that described in Example 1.

Platinum Deposition

The platinum is deposited by excess impregnation of the IZM-2/alumina support according to the same process as that described in Example 1.

The Pt content measured by XRF on the calcined catalyst is 0.20% by weight, its dispersion measured by $H_2/O_2$ assay is 83%, and its coefficient of distribution measured by Castaing microprobe is 0.98.

Example 4 (not in Accordance with the Invention): Preparation of the Catalyst D

Synthesis of Zeolite IZM-2

Zeolite IZM-2 was synthesized in accordance with the teaching of patent FR 2 918 050 B. A colloidal silica suspension known under the trade name Ludox HS-40, sold by Aldrich, is incorporated into a solution composed of sodium hydroxide (Prolabo), 1,6-bis(methylpiperidinium) hexane dibromide structuring agent, aluminium hydroxide (Aldrich) and deionized water. The molar composition of the mixture is as follows: 1 $SiO_2$, 0.0076 $Al_2O_3$, 0.1666 $Na_2O$, 0.1666 1,6-bis(methylpiperidinium)hexane, 33.3333 $H_2O$. The mixture is stirred vigorously for 30 minutes. The mixture is then transferred, after homogenization, into a Parr autoclave. The autoclave is heated for 5 days at 170° C. with spindle stirring (30 rpm). The product obtained is filtered, washed with deionized water to reach neutral pH and then dried overnight at 100° C. in an oven. The crude synthesis IZM-2 zeolite then undergoes calcination at 550° C. for ten hours (temperature increase gradient of 5° C./min) in a bed through which dry air passes (2 standard litres per hour and per gram of solid). The solid obtained is refluxed for 4 hours in an ammonium nitrate solution (10 ml of solution per gram of solid, ammonium chloride concentration of 10M) so as to exchange the alkali metal cations with ammonium ions. This refluxing step is performed four times. The solid is then filtered off, washed with deionized water and dried in an oven overnight at 100° C. Finally, to obtain the zeolite in its proton (acid) form, a step of calcination is performed at 550° C. for 10 hours (temperature increase gradient of 5° C./minute) in a bed through which dry air passes (2 standard litres per hour and per gram of solid). The solid thus obtained was analysed by X-ray diffraction and identified as being constituted by zeolite IZM-2. Characterizations by $^{27}$Al NMR, X-ray fluorescence and atomic absorption make it possible to obtain the following results for IZM-2:

weight percentage of hexacoordinated aluminium atoms $Al^{VI}$: 8%,
  ratio of the number of moles of silicon divided by the number of moles of network aluminium, in mol/mol, Si/Al: 58,
  ratio of the number of moles of silicon divided by the number of moles of overall aluminium, in mol/mol, measured by X-ray fluorescence: 53
  ratio of the number of moles of sodium divided by the number of moles of network aluminium, in mol/mol, Si/Al: 0.05.

Preparation of the IZM-2/Alumina Support

The IZM-2/alumina support is obtained according to the same process as that described in Example 1.

Platinum Deposition

The platinum is deposited by excess impregnation of the IZM-2/alumina support according to the same process as that described in Example 1.

The Pt content measured by XRF on the calcined catalyst is 0.21% by weight, its dispersion measured by $H_2/O_2$ assay is 80%, and its coefficient of distribution measured by Castaing microprobe is 0.97.

Example 5 (not in Accordance with the Invention): Preparation of the Catalyst E

Synthesis of Zeolite IZM-2

Zeolite IZM-2 was synthesized in accordance with the teaching of patent application FR 2 918 050 A. A colloidal silica suspension known under the trade name Ludox HS-40, sold by Aldrich, is incorporated into a solution composed of sodium hydroxide (Prolabo), 1,6-bis(methylpiperidinium) hexane dibromide structuring agent, aluminium hydroxide (Aldrich) and deionized water. The molar composition of the mixture is as follows: 1 $SiO_2$, 0.0060 $Al_2O_3$, 0.1666 $Na_2O$, 0.1666 1,6-bis(methylpiperidinium)hexane dibromide, 33.3333 $H_2O$. The mixture is stirred vigorously for 30 minutes. The mixture is then transferred, after homogenization, into a Parr autoclave. The autoclave is heated for 5 days at 170° C. with spindle stirring (30 rpm). The product obtained is filtered, washed with deionized water to reach neutral pH and then dried overnight at 100° C. in an oven. The solid is then introduced into a muffle furnace and calcined so as to remove the structuring agent. The calcination cycle comprises a temperature rise up to 200° C., a stationary phase of two hours at this temperature, a temperature rise up to 550° C., followed by a stationary phase of eight hours at this temperature and finally a return to ambient temperature. The temperature rises are performed with a gradient of 2° C./minute. The solid thus obtained is then refluxed for 2 hours in aqueous ammonium nitrate solution (10 ml of solution per gram of solid, ammonium nitrate concentration of 3M) so as to exchange the sodium alkaline cations with ammonium ions. This refluxing step is performed four times with fresh ammonium nitrate solution, and the solid is then filtered off, washed with deionized water and dried in an oven overnight at 100° C. Finally, to obtain the zeolite in its acid (protonated H+) form, a step of calcination is performed at 550° C. for 10 hours (temperature increase gradient of 2° C./minute) in a traversed bed under dry air (2 standard litres per hour and per gram of solid). The solid thus obtained was analysed by X-ray diffraction and identified as being constituted by zeolite IZM-2. Characterizations via the $^{27}$Al NMR, X-ray fluorescence and ICP methods afford the following results for IZM-2:

weight percentage of hexacoordinated aluminium atoms $Al^{VI}$: 5%,
  ratio of the number of moles of silicon divided by the number of moles of network aluminium, in mol/mol, Si/Al: 72,
  ratio of the number of moles of sodium divided by the number of moles of network aluminium, in mol/mol, Na/Al: 0.03.

Preparation of the IZM-2/Alumina Support

The IZM-2/alumina support is obtained according to the same process as that described in Example 1.

Platinum Deposition

The platinum is deposited by excess impregnation of the IZM-2/alumina support according to the same process as that described in Example 1.

The Pt content measured by XRF on the calcined catalyst is 0.20% by weight, its dispersion measured by $H_2/O_2$ assay is 83%, and its coefficient of distribution measured by Castaing microprobe is 0.95.

Example 6: Evaluation of the Catalytic Properties of Catalysts B and C in Accordance with the Invention and a, D and E not in Accordance with the Invention, in the Isomerization of a Paraffinic Feedstock The catalysts were tested in the isomerization of a paraffinic feedstock composed of n-hexadecane. The tests were performed in a micro-unit using a fixed-bed reactor and working in a descending stream without recycling. The analysis of the hydrocarbon-based effluents is performed online by gas chromatography. Once charged into the unit, the catalyst undergoes a first step of drying under nitrogen under the following conditions:

nitrogen flow rate: 2 standard litres per hour and per gram of catalyst,
  total pressure: 0.1 MPa,
  temperature increase gradient from ambient temperature to 150° C.: 5° C./min,
  stationary phase at 150° C. for 30 minutes.

After drying, the nitrogen is replaced with hydrogen and a step of reduction under a flow of pure hydrogen is then performed under the following conditions:

hydrogen flow rate: 5 standard litres per hour and per gram of catalyst,
  total pressure: 1.1 MPa,
  temperature increase gradient from 150 to 450° C.: 5° C./min,
  stationary phase at 450° C. for 1 hour.

After the reduction step, the temperature is reduced to 230° C. and the catalyst is placed in contact with n-hexadecane under the following conditions:

hourly space velocity of 2 grams of n-hexadecane per hour and per gram of catalyst,
  hydrogen partial pressure of 1.0 MPa
  total pressure of 1.1 MPa.

The conversion is modified by varying the temperature; and at each temperature stationary phase, two analyses of the effluent are performed, which makes it possible to calculate the catalytic performance and to check the stability of the catalytic performance for said temperature stationary phase. Typically, the temperature is varied between 230 and 350° C. in temperature stationary phases of 5° C. The analysis of the effluents is performed integrally by means of an online GC system. The temperature required to reach 50% conversion serves as a descriptor of the activity of the catalyst, while the maximum yield of hexadecane isomers obtained serves as a descriptor of the isomerizing properties of the catalyst.

TABLE 1 catalytic performance qualities of catalysts A, B, C, D and E in the hydroconversion of n-hexadecane

| Catalyst | A (not in accordance) | B (in accordance) | C (in accordance) | D (not in accordance) | E (not in accordance) |
|---|---|---|---|---|---|
| Temperature at 50% conversion (° C.) | 233 | 253 | 258 | 262 | 269 |
| Max yield of isomers (weight %) | 57 | 84 | 85 | 85 | 84 |

It is noted that catalysts B and C in accordance with the invention have comparable isomerizing properties but higher activities than those of catalysts D and E not in accordance with the invention. Catalysts B and C in accordance with the invention have lower activities but greater isomerizing properties than those of catalyst A not in accordance with the invention.

The invention claimed is:

1. Process for isomerization of a paraffinic feedstock having between 9 and 25 carbon atoms, said paraffinic feedstock been produced from renewable resources selected from plant oils, oils of algae or algal oils, fish oils and fats of plant or animal origin, or mixtures thereof, or by a process comprising upgrading the paraffinic feedstock via a Fischer-Tropsch route,
wherein the isomerization process operates at a temperature of between 200° C. and 500° C., at a total pressure of between 0.45 MPa and 7 MPa, at a hydrogen partial pressure of between 0.3 and 5.5 MPa, at an hourly space velocity of between 0.1 and 10 kilograms of paraffinic feedstock introduced per kilogram of catalyst and per hour and with a catalyst comprising at least one metal of group VIII of the periodic table of elements, at least one matrix and a IZM-2 zeolite,
wherein a molar ratio of silicon to network aluminium of the IZM-2 zeolite is between 25 and 55.

2. Process according to claim 1, in which the molar ratio of silicon to network aluminium of the IZM-2 zeolite is between 25 and 50.

3. Process according to claim 1, in which the molar ratio of silicon to network aluminium of the IZM-2 zeolite is between 30 and 50.

4. Process according to claim 1, in which said matrix is aluminates or said matrix is selected from alumina, silica, silica-alumina, clays, titanium oxide, boron oxide, zirconia, and mixtures thereof.

5. Process according to claim 1, in which the metal of group VIII is selected from iron, cobalt, nickel, ruthenium, rhodium, palladium, osmium, iridium and platinum.

6. Process according to claim 5, in which the metal of group VIII is selected from the noble metals of group VIII.

7. Process according to claim 6, in which the noble metal content of said catalyst is between 0.01% and 5% by weight relative to the total weight of said catalyst.

8. Process according to claim 6, wherein the metal from said noble metals of group VIII is selected from palladium and platinum.

9. Process according to claim 1, comprising at least one additional metal selected from metals of groups IIIA, IVA and VIIB of the periodic table of elements.

10. Process according to claim 9 wherein the metals of groups IIIA, IVA and VIIB of the periodic table of elements are selected from gallium, indium, tin and rhenium.

11. Process according to claim 1, in which said process is carried out at a temperature of between 200° C. and 450° C., at a total pressure of between 0.6 MPa and 6 MPa, at a hydrogen partial pressure of between 0.4 and 4.8 MPa, and at an hourly space velocity of between 0.2 and 7 kilograms of feedstock introduced per kilogram of catalyst and per hour.

* * * * *